(12) United States Patent
Besson et al.

(10) Patent No.: US 9,499,506 B2
(45) Date of Patent: Nov. 22, 2016

(54) METHOD FOR PREPARING 2,5-FURANDICARBOXYLIC ACID

(71) Applicants: CENTRE NATIONAL DE LA RECHERCHE SCIENTIFIQUE (C.N.R.S), Paris (FR); UNIVERSITE CLAUDE BERNARD LYON 1, Villeurbanne (FR)

(72) Inventors: Michele Besson, Les Echets (FR); Nadine Essayem, Saint Just Chaleyssin (FR); Hicham Ait Rass, Villeurbanne (FR)

(73) Assignees: CENTRE NATIONAL DE LA RECHERCHE SCIENTIFIQUE (C.N.R.S), Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 14/766,869

(22) PCT Filed: Feb. 11, 2014

(86) PCT No.: PCT/EP2014/052622
§ 371 (c)(1),
(2) Date: Aug. 10, 2015

(87) PCT Pub. No.: WO2014/122319
PCT Pub. Date: Aug. 14, 2014

(65) Prior Publication Data
US 2015/0376154 A1 Dec. 31, 2015

(30) Foreign Application Priority Data
Feb. 11, 2013 (FR) ...................................... 13 51138

(51) Int. Cl.
*C07D 307/48* (2006.01)
*B01J 23/18* (2006.01)
*B01J 23/42* (2006.01)
*B01J 23/644* (2006.01)
*C07D 307/68* (2006.01)
*B01J 21/18* (2006.01)

(52) U.S. Cl.
CPC .............. *C07D 307/68* (2013.01); *B01J 21/18* (2013.01); *B01J 23/6447* (2013.01)

(58) Field of Classification Search
CPC ....... C07D 307/48; B01J 23/18; B01J 23/42; B01J 23/6447
See application file for complete search history.

(56) References Cited

U.S. PATENT DOCUMENTS

| 2,407,066 A | 9/1946 | Dunlop | |
| 2008/0103318 A1* | 5/2008 | Linga et al. ......... | C07D 307/68 549/485 |

FOREIGN PATENT DOCUMENTS

| FR | 2 669 634 A1 | | 5/1992 | |
| WO | 2011/043660 A2 | | 4/2011 | |
| WO | 2012/017052 A1 | | 2/2012 | |
| WO | WO 2012/017052 | * | 2/2012 | ........... C07D 307/68 |

OTHER PUBLICATIONS

Vinke, Oxidation of Carbohydrates and Derivatives Using Carbon Supported Noble Metal Catalysts, pp. 1-151, XP055087077 (1991).*
Peter Vinke: "Oxidation of carbohydrates and derivatives using carbon supported noble metal catalysts",Nov. 21, 1991, pp. 1-151, XP055087077, Delft, NL Retrieved from the Internet: URL:http://repository.tudelft.nl/view/ir/u uid:c4187a70-7b13-4908-bca9-ea5f8da51409/ [retrieved on Nov. 7, 2013] table 1 pp. 111,119.
Kroeger M et al.: "A new approach for the production of 2,5-furandicarboxylic acid by in situ oxidation of 5-hydroxymethylfurfural starting from fructose", Topics in Catalysis, Baltzer Science Publishers, Bussum, NL, vol. 13, Jan. 1, 2000, pp. 237-242, XP002471377, ISSN: 1022-5528, DOI: 10.1023/A:1009017929727 cited in the application the whole document.
Michael A Lilga et al.: "Production of Oxidized Derivatives of 5-Hydroxymethyl furfural (HMF)", Topics in Catalysis, Kluwer Academic Publishers-Plenum Publishers, NE, vol . 53, No. 15-18, May 28, 2010, pp. 1264-1269, XP019831620, ISSN: 1572-9028 p. 1269.
International Search Report, dated Apr. 7, 2014, from corresponding PCT application.

* cited by examiner

*Primary Examiner* — Erich A Leeser
(74) *Attorney, Agent, or Firm* — Young & Thompson

(57) ABSTRACT

A method for preparing 2,5-furandicarboxylic acid (FDCA) by oxidizing 5-hydroxymethylfurfural (HMF) in water in the presence of a weak base and a supported catalyst comprising platinum and bismuth, in which the Bi/Pt molar ratio in the catalyst is between 0.1 and 0.3, and preferably between 0.15 and 0.3.

13 Claims, No Drawings

METHOD FOR PREPARING 2,5-FURANDICARBOXYLIC ACID

The present invention concerns a method for preparing 2,5-furandicarboxylic acid (FDCA) by oxidising 5-hydroxymethylfurfural (HMF).

FDCA is a compound of importance in the chemical industry, particularly for the polymer industry. FDCA can be used as basic monomer for the preparation in particular of polyamide or polyester.

FDCA is particularly used as basic monomer for the preparation of polyethylene furandicarboxylate (PEF). However, PEF is described as possibly being a bio-derived polymer able to replace polyethylene terephthalate (PET) (Energy Environ. Sci., 2012, 5, 6407-6422) obtained from terephthalic acid derived from fossil sources.

Therefore FDCA obtained from HMF which itself can be obtained by dehydrating fructose, is a bio-based compound of choice which could replace fossil-sourced compounds.

There is therefore a major interest in providing a method for preparing FDCA from HMF.

Various methods are known (US2008/0103318 and WO2012/017052) for preparing FDCA by oxidising HMF in an aqueous alkaline solution in the presence of a supported platinum catalyst, carbon-supported platinum in particular, and a weak base. In the first process, low HMF/Pt ratios are required (use of high amounts of platinum) in a continuous reactor to obtain a good yield, which increases the cost of implementing the process. In the second method the oxidant is pure oxygen under pressure and the reactor is a semi-closed reactor.

It has been proposed to modify the catalyst by adding lead (FR2669634 and Verdeguer et al., Journal of Molecular Catalysis, 1993, 85, 327-344). However the processes are then conducted in the presence of a strong base. In addition, the amounts of lead added are high and are not fully deposited on the catalytic solid which may give rise to a non-negligible pollution problem.

Given the instability of HMF in the aqueous acid medium for used for its synthesis, a method has also been proposed to prepare FDCA from fructose, a method whereby the oxidation step of HMF—previously obtained by dehydration of fructose in the presence of an acid catalyst—to FDCA is performed in an organic solvent medium (methylisobutyl ketone) in the presence of a carbon-supported platinum bismuth catalyst (PtBi/C) wherein the Bi/Pt molar ratio is 1 (M. Kröger et al., Topics in Catalysis, 2000, 13, 237-242). This method has the disadvantage of requiring the use of an organic solvent and also a high quantity of bismuth. In addition, the yield of the oxidation step is low.

Finally a method has recently been proposed (WO2011/043660) to prepare FDCA from fructose comprising the conversion of the fructose to an HMF ether in an alcohol solvent, followed by oxidation of the formed HMF ethers to FDCA. Oxidation takes place in an acetic acid medium at 130° C. in the presence of a soluble catalyst comprising cobalt and manganese and in the presence of bromic acid. The conditions for implementing oxidation are therefore complex due in particular to the use of bromide and acetic acid. In addition, since the catalyst is soluble, the recycling thereof is therefore not possible. The FDCA yield is about 80%.

There is therefore a particular interest in providing a method to prepare FDCA from HMF requiring neither an organic solvent, nor a strong base, nor a bromide compound.

It is one objective of the invention to provide a method for preparing FDCA by oxidising HMF with air in water.

It is another objective to provide a method for preparing FDCA which does not require the use of an organic solvent and bromide compound.

It is another objective of the present invention to provide a method for preparing FDCA allowing good yields to be obtained, in particular quantitative yields with short reaction time.

A further objective of the invention is to provide a method for preparing FDCA which uses a solid catalyst that can easily be recycled without the need for pre-treatment.

Other objectives will become apparent in the light of the following description of the invention.

The aforementioned objectives are met with the present invention which concerns a method to prepare 2,5-furane dicarboxylic acid (FDCA) comprising the oxidation of 5-hydroxymethylfurfural (HMF) in water in the presence of a weak base and a supported catalyst comprising platinum and bismuth.

In the present invention by <<weak base>> is meant a base having a pKb higher than 1.4, preferably between 3 and 10, for example between 3 and 8 at 25° C. in dilute solution. The weak base can be selected in particular from the carbonates and hydrogen carbonates of alkaline metals, sodium and potassium in particular, either alone or in a mixture. Preferably the base is sodium carbonate.

The use of a weak base advantageously allows limiting of secondary reactions, particularly HMF decomposition and Cannizzaro reactions which can occur in a strongly alkaline medium (strong base). The use of a weak base also advantageously allows FDCA to be obtained in salt form which prevents its adsorption on the surface of the catalyst and hence poisoning of the catalyst whilst maintaining a favourable pH for the reaction.

In the invention, and unless otherwise indicated, the expression <<between xxx and yyy>> is to be construed as including the limits xxx and yyy.

Oxidation can be carried out in any manner known to persons skilled in the art and in particular under pressurized air or oxygen, preferably under air pressure. Preferably, the air or oxygen pressure applied is such that the $O_2$/HMF molar ratio is higher than 2. The pressure may in particular range from 20 to 60 bar (2 to 6 MPa) air pressure, preferably 30 to 50 bar (3 to 5 MPa), for example 40 bar air pressure (4 MPa). The oxygen partial pressure may be 4 to 12 bar, preferably 6 to 10 bar, e.g. 8 bar.

The method can be conducted at a temperature of 70 to 150° C., preferably 80 to 120° C., e.g. 100° C.

The catalyst of the invention is a catalyst comprising platinum and bismuth on a support. The catalyst of the invention is called PtBi/support in the remainder hereof.

Advantageously, the presence of bismuth provides the platinum with protection against over-oxidation. As a result and advantageously, the catalyst of the invention can be re-used several times without the need for prior subjection to reduction, contrary to a monometallic catalyst. This can in particular allow an increase in the yield of an industrial plant.

The catalyst support can be selected from among all supports known to those skilled in the art and more particularly from among supports stable in water and preferably in a basic medium. The support is preferably selected from among activated carbon, carbons, metal oxides or lanthanide oxides stable in aqueous media, in particular basic aqueous media, e.g. the oxides of zirconium, titanium, cerium, or mixture thereof. Preferably the support is activated carbon.

The catalyst of the invention can be prepared using any method known to persons skilled in the art.

Preferably the catalyst is prepared in two steps, a first step to prepare a supported platinum and a second step to add bismuth; such methods have been described for example by T. Mallat, A. Baiker (Chem. Rev. 2004, 104, 3037).

Preferably, the first step is performed by liquid phase impregnation of the support with an aqueous platinum solution, in particular an aqueous $H_2PtCl_6$ solution, followed by reduction with a formaldehyde solution in a basic medium. The final PtBi/support catalyst of the invention is prepared from the supported platinum obtained at the first step:

- either in situ, in the reaction medium comprising the supported platinum during HMF oxidation, by adding an aqueous solution of a soluble bismuth salt in particular bismuth nitrate $Bi(NO_3)_3.5H_2O$;
- or ex situ by adding to the supported platinum an aqueous solution of a soluble bismuth salt comprising a reducer e.g. glucose, in particular bismuth oxynitrate ($BiONO_3$).

In both these cases the PtBi/support catalyst is obtained by surface oxidation-reduction reaction between the supported platinum and the bismuth salt in aqueous solution.

Preferably the amount of platinum in the catalyst is between 1% and 10%, preferably between 3% and 6% by weight relative to the total weight of the supported catalyst.

Preferably, in the catalyst of the invention the Bi/Pt molar ratio is between 0.05 and 2.5, preferably between 0.1 and 0.3, e.g. between 0.15 and 0.3. Advantageously these ranges of Bi/Pt molar ratio allow a quantitative or near-quantitative yield to be obtained, in particular 95% or higher, even 99% or higher, in a reduced reaction time. On account of the sensitivity of HMF in a basic aqueous solution, a method must be used which allows total or almost total conversion in a short time. Therefore, advantageously the method is conducted for 1 h to 10 h, preferably for 2 h to 4 h. The aforementioned ranges of Bi/Pt molar ratio allow a better compromise to be obtained between reaction time and FDCA yield. Outside these ranges a longer reaction time is needed to obtain a quantitative FDCA yield, thereby increasing risks of HMF degradation.

The method of the present invention is preferably conducted with a weak base/HMF molar ratio of 1 or higher, preferably between 2 and 6, for example between 2 and 4.

The method of the present invention is preferably conducted with a HMF/Pt molar ratio of between 50 and 400, preferably between 100 and 200. Advantageously the presence of bismuth in the catalyst of the invention, which provides protection for the platinum against over-oxidation and in particular within the above-specified ratios, also limits the amount of platinum to be used in the method of the invention. The method of the invention thereby becomes more economical and more environmental compared with prior art methods.

The method of the invention is conducted in water. It must therefore be understood that the reaction medium does not contain any organic solvent.

In particularly preferred manner in the method of the invention the weak base is calcium or potassium carbonate and the Bi/Pt molar ratio is between 0.05 and 2.5, preferably it is between 0.1 and 0.3, for example it is between 0.15 and 0.3.

The method of the present invention can be performed with batch or continuous operation. In one advantageous embodiment the method is carried out continuously.

A description is now given of the present invention with the help of non-limiting examples.

Method for Preparing the Catalysts

The carbons used for preparing the catalysts were L3S and 3SW carbons made by CECA.

The method applied was the method described by Dirkx and Van Der Baan (J. M. H. Dirkx and H. S. van Der Baan, Journal of Catalysis 67 (1981) 1-13).

5.1% Pt/C(3SW) Catalyst

In a 250 mL three-necked round-bottom flask 10 g of CECA 3SW carbon was placed in suspension in 100 mL of ultrapure water at ambient temperature under a stream of nitrogen and under agitation. A 12 mL aqueous solution containing 1.7 g of the metal precursor ($H_2PtCl_6$, $6H_2O$) was added dropwise. Impregnation was conducted at ambient temperature for 5 hours. The suspension was then cooled down to a temperature below 5° C. Reduction of the catalyst was carried out in liquid phase through the dropwise addition of 50 mL aqueous formaldehyde (37% by weight in water) for 20 min, followed by the careful addition of 20 mL of 30% KOH solution so as to maintain the temperature below 5° C. Reduction was left to continue overnight at ambient temperature under continued nitrogen bubbling. Finally, the suspension was filtered and washed to neutrality of the filtrate. The recovered catalyst was dried under a stream of nitrogen at 80° C. for one day. After drying the catalyst was stored in an inert atmosphere.

The 3.6% Pt/C (L3S) catalyst was prepared in similar manner on L3S carbon.

The bimetallic catalysts (PtBi/C) were prepared either ex-situ from the monometallic catalyst (Pt/C) prepared following the above-described method, by depositing bismuth via redox reaction between the Pt surface and the bismuth oxide in the presence of glucose as reducer. The reaction was conducted 40° C. under a stream of nitrogen and magnetic agitation for 1 h. The catalysts can also be prepared in-situ during the oxidation reaction by adding an amount of bismuth salt (corresponding to the desired Bi/Pt ratio).

5.1% Pt1% Bi/C(3SW) Catalyst—Ex Situ

In a 500 mL three-necked round-bottom flask equipped with magnetic bar and nitrogen bubbling system, 5 g of monometallic 5.1% Pt/C(3SW) catalyst were placed in suspension in 300 mL of ultrapure water. The suspension was heated to a temperature of 40° C. using a hot plate equipped with a thermocouple and water bath. After 20 minutes, 186 g of glucose were added (corresponding to a glucose/Pt molar ratio of 790) using a funnel for solids and the suspension was left under agitation for 10 minutes. A solution of bismuth oxynitrate (0.06 g $BiONO_3$ solubilised in 3 mL of 1M HCl solution) was then added dropwise. After an agitation time of about 1 hour the heating was stopped and the system cooled. The suspension was neutralised through the addition of 0.2 M NaOH solution to reach a pH of more than 9. The suspension was finally filtered and washed to neutrality of the filtrate. The recovered catalyst was dried under a stream of nitrogen at 80° C. for one day. After drying the catalyst was stored in an inert atmosphere.

The other catalysts with different Bi/Pt ratios were prepared in the same manner by adjusting the amount of bismuth salt in accordance with the following table per 1 g of prepared bimetallic catalyst.

| Catalyst | Pt/C used in the method | Quantity of $BiONO_3$ [mg] | Bi/Pt Ratio |
| --- | --- | --- | --- |
| 5% Pt0.4% Bi/C(3SW) | 5.1% Pt/C(3SW) | 6 | 0.07 |
| 5% Pt0.7% Bi/C(3SW) | 5.1% Pt/C(3SW) | 8 | 0.13 |

-continued

| Catalyst | Pt/C used in the method | Quantity of BiONO₃ [mg] | Bi/Pt Ratio |
|---|---|---|---|
| 5.1% Pt1% Bi/C(3SW) | 5.1% Pt/C(3SW) | 11 | 0.20 |
| 3.6% Pt0.9% Bi/C(L3S) | 3.6% Pt/C(L3S) | 10 | 0.25 |
| 4.5% Pt1.65% Bi/C(3SW) | 5.1% Pt/C(3SW) | 20 | 0.36 |
| 3.6% Pt1.9% Bi/C(L3S) | 3.6% Pt/C(L3S) | 19 | 0.52 |
| 3.5% Pt3.4% Bi/C(L3S) | 3.6% Pt/C(L3S) | 39 | 0.96 |

3.6% Pt0.68% Bi/C(L3S) Catalyst—In Situ 15 mg of bismuth salt (Bi(NO₃)₃, 5H₂O), corresponding to a Bi/Pt molar ratio of 0.2, were placed in the reactor in 150 mL of 0.2 M Na₂CO₃ solution. 0.816 g of the monometallic catalyst 3.6% Pt/C(L3S) were added. After closing the reactor, the suspension was placed under agitation in an inert atmosphere for 1 hour. 2 g of HMF were then added and the catalytic test was directly initiated following the standard protocol described below. On completion of the reaction the catalyst was recovered and analysed.

Experimental Conditions

The HMF having 95% purity was supplied by Interchim.

The method of the invention was implemented in a discontinuous reactor under pressure in a 300 mL autoclave equipped with magnetically driven gas-inducing agitator. Heating was ensured by a heating collar connected to a PID controller (proportional integral derivative). A sampling gate allowed the taking of a sample from the reaction medium via an immersed tube, allowing the monitoring of the progress of the reaction over time. The samples were analysed by HPLC chromatography with two RID detectors (Refractive Index Detector) and PDA (Photodiode array) (ICE-Coragel 107H column, eluting with 10 mM H₂SO₄). Total Organic Carbon (TOC) in solution was also analysed using a TOC analyser and the value measured was compared with the mass balance (MB) calculated by HPLC.

The reactor was charged with 150 mL of 100 mM aqueous HMF solution (2 g), a weight of catalyst corresponding to a HMF/Pt molar ratio of 100, and the desired amount of base in the form of NaOH (comparative example), NaHCO₃, KHCO₃, Na₂CO₃ or K₂CO₃ expressed as base/HMF molar ratio. Air was added at a pressure of 40 bar and the reactor heated to 100° C.

EXAMPLE 1 (COMPARATIVE)

Monometallic Catalysts in the Presence of NaHCO₃

The above-described reaction was conducted in the presence of two Pt catalysts supported on two types of carbon (CECA L3S and 3SW) with a NaHCO₃/HMF molar ratio of 4.

The results are given in Tables 1 and 2 below.

TABLE 1

| 3.6% Pt/C(L3S) | | | | | | | |
|---|---|---|---|---|---|---|---|
| Time [h] | pH | HMF [mM] | HMFCA [mM] | DFF [mM] | FFCA [mM] | FDCA [mM] | MB [mM] | TOC [mM] |
| 0 | 8.64 | 99 | 0 | 0 | 0 | 0 | 99 | 100 |
| 0.25 | 8.57 | 52 | 5 | 3 | 31 | 1 | 91 | |
| 0.5 | 8.39 | 8 | 7 | 0 | 68 | 8 | 91 | |
| 1 | 8.25 | 1 | 5 | 0 | 68 | 20 | 94 | |
| 2 | 8.15 | 0 | 2 | 0 | 53 | 39 | 95 | 94 |
| 3 | 8.22 | 0 | 0 | 0 | 43 | 50 | 94 | |
| 4 | 8.25 | 0 | 0 | 0 | 34 | 61 | 95 | |

TABLE 1-continued

| 3.6% Pt/C(L3S) | | | | | | | |
|---|---|---|---|---|---|---|---|
| Time [h] | pH | HMF [mM] | HMFCA [mM] | DFF [mM] | FFCA [mM] | FDCA [mM] | MB [mM] | TOC [mM] |
| 5 | 8.19 | 0 | 0 | 0 | 29 | 66 | 95 | |
| 6 | 8.07 | 0 | 0 | 0 | 23 | 72 | 95 | 96 |
| 8 | 8.03 | 0 | 0 | 0 | 14 | 81 | 95 | |
| 10 | 7.68 | 0 | 0 | 0 | 8 | 88 | 96 | |
| 12 | 7.52 | 0 | 0 | 0 | 5 | 90 | 96 | 94 |

TABLE 2

| 5.1% Pt/C(3SW) | | | | | | | |
|---|---|---|---|---|---|---|---|
| Time [h] | pH | HMF [mM] | HMFCA [mM] | DFF [mM] | FFCA [mM] | FDCA [mM] | MB [mM] | TOC [mM] |
| 0 | 8.61 | 100 | 0 | 0 | 0 | 0 | 100 | 94 |
| 0.25 | 8.51 | 42 | 5 | 3 | 40 | 2 | 92 | |
| 0.5 | 8.51 | 16 | 8 | 2 | 62 | 6 | 94 | |
| 1 | 8.42 | 1 | 7 | 0 | 71 | 18 | 96 | |
| 2 | 8.35 | 0 | 4 | 0 | 59 | 34 | 97 | 97 |
| 3 | 8.33 | 0 | 2 | 0 | 48 | 47 | 97 | |
| 4 | 8.31 | 0 | 0 | 0 | 41 | 55 | 96 | |
| 5 | 8.25 | 0 | 0 | 0 | 34 | 62 | 96 | |
| 6 | 8.33 | 0 | 0 | 0 | 28 | 69 | 97 | 96 |
| 8 | 8.43 | 0 | 0 | 0 | 21 | 77 | 97 | |
| 10 | 8.24 | 0 | 0 | 0 | 14 | 83 | 97 | |
| 12 | 8.09 | 0 | 0 | 0 | 9 | 89 | 98 | 96 |

The results show that the conversion of HMF is rapid, in less than 1 h, to give as intermediates 2,5-diformylfuran (DFF) and 5-hydroxymethyl-2-furan carboxylic acid (HMFCA) which are easily oxidised to 2-formyl-5-furan carboxylic acid (FFCA). Oxidation of the aldehyde function of FFCA to give FDCA was much slower. After 24 h reaction time, FFCA conversion was complete and the yield of FDCA was quantitative. The type of carbon support (acid pH for L3S and base pH for 3SW, according to supplier's data) did not have any influence on the activity of the catalysts.

The reaction was conducted with NaOH as base instead of NaHCO₃. Under these conditions the HMF was rapidly degraded.

EXAMPLE 2 (COMPARATIVE)

Influence of the Type of Base in the Presence of a Monometallic Pt/C Catalyst

The above-described reaction was conducted in the presence of a 5.1% Pt/C(3SW) catalyst and two weak bases, NaHCO₃ and K₂CO₃, with base/HMF ratios of 4 and 2 respectively.

The results are grouped together in Tables 3 and 4 below.

TABLE 3

| NaHCO₃/HMF molar ratio of 4 | | | | | | |
|---|---|---|---|---|---|---|
| Time [h] | HMF [mM] | % C HMF | FFCA [mM] | % Y FFCA | FDCA [mM] | % Y FDCA |
| 0 | 100 | 0 | 0 | 0 | 0 | 0 |
| 0.25 | 42 | 58 | 40 | 40 | 2 | 2 |
| 0.5 | 16 | 84 | 62 | 62 | 6 | 6 |
| 1 | 1 | 99 | 71 | 71 | 18 | 18 |
| 2 | 0 | 100 | 59 | 59 | 34 | 34 |
| 3 | 0 | 100 | 48 | 48 | 47 | 47 |
| 4 | 0 | 100 | 41 | 41 | 55 | 55 |

TABLE 3-continued

NaHCO₃/HMF molar ratio of 4

| Time [h] | HMF [mM] | % C HMF | FFCA [mM] | % Y FFCA | FDCA [mM] | % Y FDCA |
|---|---|---|---|---|---|---|
| 5 | 0 | 100 | 34 | 34 | 62 | 62 |
| 6 | 0 | 100 | 28 | 28 | 69 | 69 |
| 8 | 0 | 100 | 21 | 21 | 77 | 77 |
| 10 | 0 | 100 | 14 | 14 | 83 | 83 |
| 12 | 0 | 100 | 9 | 9 | 89 | 89 |

(% Y FFCA = yield (%) of FFCA, % Y FDCA = yield (%) of FDCA % C = conversion (%) of HMF)

TABLE 4

K₂CO₃/HMF molar ratio of 2

| Time [h] | HMF [mM] | % C HMF | FFCA [mM] | % Y FFCA | FDCA [mM] | % Y FDCA |
|---|---|---|---|---|---|---|
| 0 | 96 | 0 | 0 | 0 | 0 | 0 |
| 0.25 | 25 | 73 | 38 | 39 | 13 | 13 |
| 0.5 | 0 | 99 | 45 | 47 | 32 | 34 |
| 1 | 0 | 100 | 34 | 35 | 49 | 51 |
| 2 | 0 | 100 | 23 | 24 | 63 | 66 |
| 3 | 0 | 100 | 18 | 18 | 71 | 73 |
| 4 | 0 | 100 | 13 | 14 | 78 | 81 |
| 6 | 0 | 100 | 9 | 9 | 83 | 86 |
| 8 | 0 | 100 | 6 | 6 | 87 | 90 |
| 10 | 0 | 100 | 4 | 4 | 89 | 93 |
| 12 | 0 | 100 | 3 | 3 | 91 | 94 |

(% Y FFCA = yield (%) of FFCA, % Y FDCA = yield (%) of FDCA % C = conversion (%) of HMF)

The results show that the use of a weak base stronger than NaHCO₃ (K₂CO₃ or Na₂CO₃) allows improved oxidation rates. For example, in the presence of 5.1% Pt/C(3SW) catalyst, the reaction time required to reach a quantitative yield is about 14 hours.

EXAMPLE 3 (COMPARATIVE)

Study on Recycling of the 3.6% Pt/C(L3S) Catalyst

The 3.6% Pt/C(L3S) catalyst was used for three oxidation reactions of HMF under the above-described conditions. It was used in a first HMF oxidation reaction (1$^{st}$ cycle) in the presence of 4 equivalents of NaHCO₃ (relative to HMF). After a reaction time of 24 hours, the catalyst was recovered by filtration, washed, dried in air in an oven at 100° C. and reduced under a stream of hydrogen at 350° C. for 2 hours. After this treatment step, the catalyst was again used in a second HMF oxidation reaction (2$^{nd}$ cycle) under identical conditions. It was then washed with water and dried in air in an oven at 100° C. The catalyst was then used directly (without prior reduction step) for a third HMF oxidation reaction (3$^{rd}$ cycle) under identical conditions.

The results obtained are grouped together in Table 5 for the 1$^{st}$ cycle, Table 6 for the 2$^{nd}$ cycle and Table 7 for the 3$^{rd}$ cycle.

TABLE 5

1$^{st}$ cycle

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.58 | 95 | 0 | 0 | 0 | 0 | 95 | 96 |
| 0.5 | 8.41 | 27 | 6 | 1 | 52 | 6 | 91 | |
| 1 | 8.28 | 1 | 5 | 0 | 67 | 23 | 95 | |
| 2 | 8.29 | 0 | 1 | 0 | 44 | 51 | 95 | |
| 2.7 | 8.09 | 0 | 0 | 0 | 33 | 61 | 94 | |
| 4 | 7.69 | 0 | 0 | 0 | 23 | 72 | 95 | 97 |
| 5.8 | 7.98 | 0 | 0 | 0 | 16 | 79 | 95 | |
| 8 | 7.94 | 0 | 0 | 0 | 8 | 87 | 94 | |
| 10 | 7.9 | 0 | 0 | 0 | 4 | 91 | 94 | 97 |
| 24 | 7.48 | 0 | 0 | 0 | 0 | 95 | 95 | 98 |

TABLE 6

2$^{nd}$ cycle

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.55 | 99 | 0 | 0 | 0 | 0 | 99 | 100 |
| 0.5 | 8.09 | 15 | 0 | 0 | 62 | 16 | 94 | 96 |
| 1 | 8.11 | 0 | 0 | 0 | 63 | 35 | 99 | |
| 2 | 7.83 | 0 | 0 | 0 | 41 | 58 | 99 | |
| 3 | 7.88 | 0 | 0 | 0 | 27 | 72 | 99 | |
| 4 | 7.74 | 0 | 0 | 0 | 18 | 81 | 99 | |
| 6 | 7.78 | 0 | 0 | 0 | 8 | 90 | 99 | |
| 8 | 7.69 | 0 | 0 | 0 | 3 | 97 | 100 | |
| 10 | 7.65 | 0 | 0 | 0 | 1 | 99 | 100 | 101 |
| 24 | 7.48 | 0 | 0 | 0 | 0 | 99 | 99 | 97 |

TABLE 7

3$^{rd}$ cycle

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.45 | 99 | 0 | 0 | 0 | 0 | 99 | 99 |
| 0.5 | 8.25 | 56 | 1 | 4 | 28 | 1 | 90 | 95 |
| 1 | 8.07 | 29 | 2 | 3 | 52 | 3 | 89 | |
| 2 | 7.95 | 3 | 2 | 0 | 75 | 13 | 93 | |
| 3 | 7.86 | 0 | 3 | 0 | 69 | 22 | 94 | |
| 4 | 7.86 | 0 | 2 | 0 | 62 | 32 | 95 | |
| 6 | 7.75 | 0 | 1 | 0 | 50 | 47 | 97 | |
| 8 | 7.79 | 0 | 0 | 0 | 38 | 60 | 98 | |
| 10 | 7.52 | 0 | 0 | 0 | 28 | 70 | 98 | 101 |
| 24 | 7.48 | 0 | 0 | 0 | 2 | 97 | 99 | 102 |

The results show that for the 1$^{st}$ and 2$^{nd}$ cycles the yield is quantitative after a reaction time of 10 hours. On the other hand, there is significant loss of activity at the 3$^{rd}$ cycle with a yield of only 70% after a reaction time of 10 h. The monometallic Pt/C catalyst requires a reduction step before re-use.

EXAMPLE 4 (ACCORDING TO THE INVENTION)

Influence of Modification of Monometallic Pt/C Catalysts with Bismuth

The tests were conducted with bimetallic PtBi/C catalysts prepared following the above-described protocols with Bi/Pt molar ratios varying between 0.07 and 1.

The tests in the presence of NaHCO₃ were performed with a NaHCO₃/HMF molar ratio of 4 at a temperature of 100° C. and air pressure of 40 bar.

The results are grouped together in Tables 8, 9, and 10.

TABLE 8

5.1% Pt-1% Bi/C(3SW) catalyst (Bi/Pt molar ratio = 0.2)

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.66 | 101 | 0 | 0 | 0 | 0 | 101 | 100 |
| 0.25 | 8.49 | 31 | 8 | 2 | 49 | 5 | 95 | 99.3 |
| 0.5 | 8.32 | 3 | 8 | 0 | 67 | 20 | 97 | |
| 1 | 8.37 | 0 | 4 | 0 | 52 | 43 | 98 | |
| 2 | 8.29 | 0 | 1 | 0 | 28 | 70 | 98 | |
| 3 | 8.25 | 0 | 0 | 0 | 14 | 85 | 99 | |
| 4 | 8.17 | 0 | 0 | 0 | 7 | 92 | 99 | |
| 5 | 8.17 | 0 | 0 | 0 | 3 | 97 | 99 | |
| 6 | 8.1 | 0 | 0 | 0 | 1 | 98 | 100 | 100.7 |
| 8 | 8.24 | 0 | 0 | 0 | 0 | 99 | 100 | |
| 10 | 8.12 | 0 | 0 | 0 | 0 | 100 | 100 | |
| 12 | 7.74 | 0 | 0 | 0 | 0 | 100 | 100 | 101.1 |

TABLE 9

3.6% Pt-0.9% Bi/C(L3S) - Bi/Pt = 0.25

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.61 | 95 | 0 | 0 | 0 | 0 | 95 | 92 |
| 0.16 | 8.37 | 55 | 5 | 3 | 29 | 1 | 94 | |
| 0.33 | 8.18 | 13 | 8 | 1 | 64 | 8 | 95 | 94.7 |
| 0.5 | 8.13 | 1 | 7 | 0 | 70 | 18 | 96 | |
| 0.75 | 8.15 | 0 | 5 | 0 | 63 | 29 | 97 | |
| 1 | 8.02 | 0 | 4 | 0 | 56 | 38 | 97 | 96.57 |
| 2 | 7.89 | 0 | 1 | 0 | 38 | 60 | 100 | |
| 3 | 7.85 | 0 | 0 | 0 | 19 | 80 | 99 | |
| 4 | 7.68 | 0 | 0 | 0 | 10 | 89 | 99 | 99.01 |
| 6 | 7.64 | 0 | 0 | 0 | 3 | 96 | 100 | |
| 8 | 7.70 | 0 | 0 | 0 | 1 | 99 | 100 | |
| 10 | 7.39 | 0 | 0 | 0 | 0 | 100 | 100 | 100 |
| 12 | 7.43 | 0 | 0 | 0 | 0 | 101 | 101 | 101 |

TABLE 10

4.5% Pt-1.65% Bi/C(3SW) - Bi/Pt = 0.36

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.40 | 97 | 0 | 0 | 0 | 0 | 97 | 96 |
| 0.25 | 8.27 | 50 | 6 | 3 | 32 | 2 | 93 | |
| 0.5 | 8.22 | 16 | 9 | 2 | 61 | 7 | 94 | |
| 1 | 8.36 | 0 | 7 | 0 | 68 | 19 | 94 | |
| 2 | 7.83 | 0 | 4 | 0 | 53 | 40 | 96 | 97 |
| 4 | 7.66 | 0 | 0 | 0 | 31 | 66 | 96 | |
| 6 | 7.66 | 0 | 0 | 0 | 16 | 81 | 97 | |
| 8 | 7.58 | 0 | 0 | 0 | 8 | 88 | 96 | 99 |
| 10 | 7.72 | 0 | 0 | 0 | 3 | 94 | 97 | |
| 12 | 7.39 | 0 | 0 | 0 | 0 | 96 | 96 | 97 |

The reaction in the presence of the bimetallic 5.1% Pt-1% Bi/C(3SW) catalyst (Bi/Pt ratio=0.2) was clearly much accelerated compared with the reaction in the presence of the monometallic 5.1% Pt/C(3SW) catalyst (see comparative Example 2). The conversions of HMF and FFCA were complete in less than 6 h compared with over 12 h for the monometallic Pt/C catalyst (comparative Examples 1 and 2).

The results show that the increase in the Bi/Pt ratio e.g. to 0.36 slows the reaction.

Similarly, the modification of the 3.6% Pt/C(L3S) catalyst with bismuth strongly accelerates the reaction speeds (see comparative Example 1).

The influence of the Bi/Pt ratio was also examined in the presence of $Na_2CO_3$ ($Na_2CO_3$/HMF=2). The same trend was observed when comparing a series of bimetallic catalysts having molar ratios varying between 0.07 and 1. The results are grouped together in Tables 11 to 15.

TABLE 11

5% Pt0.4% Bi/C(3SW), Bi/Pt = 0.07

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.59 | 98 | 0 | 0 | 0 | 0 | 98 | 97 |
| 0.25 | 9.44 | 11 | 11 | 0 | 54 | 15 | 91 | |
| 0.5 | 9.06 | 0 | 8 | 0 | 50 | 38 | 96 | 95 |
| 1 | 8.83 | 0 | 3 | 0 | 32 | 61 | 96 | |
| 2 | 8.66 | 0 | 1 | 0 | 16 | 79 | 96 | 95 |
| 3 | 8.44 | 0 | 0 | 0 | 10 | 85 | 95 | |
| 4 | 8.44 | 0 | 0 | 0 | 6 | 89 | 95 | 96 |

TABLE 11-continued

5% Pt0.4% Bi/C(3SW), Bi/Pt = 0.07

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 5 | 8.33 | 0 | 0 | 0 | 3 | 93 | 96 | |
| 6 | 8.41 | 0 | 0 | 0 | 2 | 94 | 96 | 96 |

TABLE 12

5% Pt0.7% Bi/C(3SW), Bi/Pt = 0.13

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.44 | 98 | 0 | 0 | 0 | 0 | 98 | 100 |
| 0.25 | 9.39 | 13 | 10 | 0 | 52 | 20 | 94 | |
| 0.5 | 8.90 | 0 | 6 | 0 | 40 | 49 | 95 | 95 |
| 1 | 8.70 | 0 | 1 | 0 | 21 | 75 | 97 | |
| 2 | 8.49 | 0 | 0 | 0 | 9 | 87 | 96 | 97 |
| 3 | 8.49 | 0 | 0 | 0 | 3 | 93 | 96 | |
| 4 | 8.47 | 0 | 0 | 0 | 1 | 96 | 97 | 99 |
| 5 | 8.61 | 0 | 0 | 0 | 1 | 96 | 97 | |
| 6 | 8.53 | 0 | 0 | 0 | 0 | 97 | 97 | 98 |

TABLE 13

5.1% Pt1% Bi/C(3SW), Bi/Pt = 0.2

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 11.05 | 96 | 0 | 0 | 0 | 0 | 96 | 96 |
| 0.1 | 10.12 | 45 | 5 | 0 | 38 | 3 | 91 | 91 |
| 0.17 | 9.51 | 8 | 10 | 0 | 59 | 17 | 95 | 95 |
| 0.33 | 9.10 | 0 | 6 | 0 | 42 | 47 | 95 | |
| 0.5 | 8.86 | 0 | 3 | 0 | 29 | 63 | 95 | 97 |
| 1 | 8.58 | 0 | 1 | 0 | 16 | 79 | 96 | 97 |
| 2 | 8.34 | 0 | 0 | 0 | 4 | 91 | 95 | |
| 3 | 8.34 | 0 | 0 | 0 | 0 | 95 | 95 | 98 |
| 4 | 8.29 | 0 | 0 | 0 | 0 | 95 | 95 | |
| 5 | 8.25 | 0 | 0 | 0 | 0 | 96 | 96 | 98 |
| 6 | 8.24 | 0 | 0 | 0 | 0 | 96 | 96 | 97 |

TABLE 14

3.6% Pt1.9% Bi/C(L3S), Bi/Pt = 0.52

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.46 | 98 | 0 | 0 | 0 | 0 | 98 | 100 |
| 0.25 | 9.55 | 21 | 11 | 0 | 47 | 14 | 93 | |
| 0.5 | 9.09 | 0 | 7 | 0 | 45 | 42 | 94 | 94 |
| 1 | 8.7 | 0 | 4 | 0 | 28 | 64 | 96 | |
| 2 | 8.36 | 0 | 1 | 0 | 12 | 84 | 97 | 97 |
| 3 | 8.43 | 0 | 0 | 0 | 5 | 91 | 96 | |
| 4 | 8.29 | 0 | 0 | 0 | 3 | 94 | 97 | 97 |
| 5 | 8.36 | 0 | 0 | 0 | 1 | 95 | 96 | |
| 6 | 8.29 | 0 | 0 | 0 | 1 | 97 | 98 | 99 |

TABLE 15

3.5% Pt3.4% Bi/C(L3S), Bi/Pt = 0.96

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.50 | 97 | 0 | 0 | 0 | 0 | 97 | 100 |
| 0.25 | 9.60 | 17 | 11 | 1 | 57 | 7 | 93 | |
| 0.5 | 9.32 | 0 | 11 | 0 | 62 | 22 | 94 | 97 |
| 1 | 9.00 | 0 | 7 | 0 | 46 | 43 | 96 | |
| 2 | 8.72 | 0 | 3 | 0 | 27 | 67 | 97 | 99 |
| 3 | 8.37 | 0 | 1 | 0 | 15 | 79 | 96 | |
| 4 | 8.33 | 0 | 1 | 0 | 10 | 86 | 96 | |
| 5 | 8.30 | 0 | 0 | 0 | 6 | 89 | 95 | |
| 6 | 8.38 | 0 | 0 | 0 | 4 | 92 | 95 | 97 |

There therefore exists an optimal range of the Bi/Pt ratio in the catalyst allowing a quantitative FDCA yield to be obtained in a short time.

EXAMPLE 5 (ACCORDING TO THE INVENTION)

Influence of the Type and Amount of Base

The type of base used and the amount of base added were also examined. The results are given:
- in Tables 16 and 17 for the 5.1% Pt-1% Bi/C(3SW) catalyst (Bi/Pt=0.2) in the presence of 4 equivalents of NaHCO$_3$ or KHCO$_3$ relative to HMF;
- in Tables 18, 19 and 20 for the 5.1% Pt-1% Bi/C(3SW) catalyst (Bi/Pt=0.2) in the presence of 2 equivalents of Na$_2$CO$_3$ or K$_2$CO$_3$ or 4 equivalents of Na$_2$CO$_3$ relative to HMF.

TABLE 16

5.1% Pt-1% Bi/C(3SW) - Bi/Pt = 0.2-4 eq NaHCO$_3$

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.66 | 101 | 0 | 0 | 0 | 0 | 101 | 100 |
| 0.25 | 8.49 | 31 | 8 | 2 | 49 | 5 | 95 | 99 |
| 0.5 | 8.32 | 3 | 8 | 0 | 67 | 20 | 97 | |
| 1 | 8.37 | 0 | 4 | 0 | 52 | 43 | 98 | |
| 2 | 8.29 | 0 | 1 | 0 | 28 | 70 | 98 | |
| 3 | 8.25 | 0 | 0 | 0 | 14 | 85 | 99 | |
| 4 | 8.17 | 0 | 0 | 0 | 7 | 92 | 99 | |
| 5 | 8.17 | 0 | 0 | 0 | 3 | 97 | 99 | |
| 6 | 8.14 | 0 | 0 | 0 | 1 | 98 | 100 | 101 |
| 8 | 8.24 | 0 | 0 | 0 | 0 | 99 | 100 | |
| 10 | 8.12 | 0 | 0 | 0 | 0 | 100 | 100 | |
| 12 | 7.74 | 0 | 0 | 0 | 0 | 100 | 100 | 101 |

TABLE 17

5.1% Pt-1% Bi/C(3SW) - Bi/Pt = 0.2-4 eq KHCO$_3$

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 8.50 | 98 | 0 | 0 | 0 | 0 | 98 | 96 |
| 0.25 | 8.42 | 28 | 8 | 2 | 48 | 6 | 92 | |
| 0.5 | 8.15 | 3 | 8 | 0 | 64 | 20 | 94 | |
| 1 | 8.18 | 0 | 4 | 0 | 48 | 43 | 95 | |
| 2 | 8.35 | 0 | 1 | 0 | 29 | 66 | 96 | 95 |
| 3 | 8.12 | 0 | 0 | 0 | 15 | 80 | 95 | |
| 4 | 8.13 | 0 | 0 | 0 | 7 | 89 | 96 | 96 |
| 5 | 7.87 | 0 | 0 | 0 | 3 | 93 | 96 | |
| 6 | 7.78 | 0 | 0 | 0 | 1 | 95 | 97 | |
| 8 | 7.60 | 0 | 0 | 0 | 0 | 97 | 97 | 98 |
| 10 | 7.50 | 0 | 0 | 0 | 0 | 97 | 97 | 98 |
| 12 | 7.50 | 0 | 0 | 0 | 0 | 97 | 97 | 98 |

TABLE 18

5.1% Pt-1% Bi/C(3SW) - Bi/Pt = 0.2-2 eq Na$_2$CO$_3$

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 11.05 | 96 | 0 | 0 | 0.0 | 0.0 | 96 | 96 |
| 0.1 | 10.12 | 45 | 5 | 0 | 37.9 | 3.2 | 91 | 91 |
| 0.17 | 9.51 | 8 | 10 | 0 | 59.2 | 17.4 | 95 | 95 |
| 0.33 | 9.10 | 0 | 6 | 0 | 42.5 | 46.6 | 95 | |
| 0.5 | 8.86 | 0 | 3 | 0 | 28.6 | 63.1 | 95 | 97 |
| 1 | 8.58 | 0 | 0 | 0 | 16.4 | 79.2 | 96 | 97 |
| 2 | 8.34 | 0 | 0 | 0 | 4.0 | 90.8 | 95 | |
| 3 | 8.34 | 0 | 0 | 0 | 0.0 | 95.0 | 95 | 98 |
| 4 | 8.29 | 0 | 0 | 0 | 0.0 | 95.3 | 95 | |
| 5 | 8.25 | 0 | 0 | 0 | 0.0 | 95.8 | 96 | 98 |
| 6 | 8.24 | 0 | 0 | 0 | 0.0 | 95.7 | 96 | 97 |

TABLE 19

5.1% Pt-1% Bi/C(3SW) - Bi/Pt = 0.2-2 eq K$_2$CO$_3$

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.99 | 98 | 0 | 0 | 0 | 0 | 86 | 85 |
| 0.25 | 9.66 | 23 | 8 | 0 | 29 | 33 | 93 | * |
| 0.5 | 8.88 | 0.0 | 4 | 0 | 21 | 72 | 96 | * |
| 1 | 8.40 | 0.0 | 0 | 0 | 8 | 88 | 96 | * |
| 2 | 8.29 | 0.0 | 0 | 0 | 1 | 95 | 97 | 98 |
| 3 | 8.33 | 0.0 | 0 | 0 | 0 | 96 | 96 | * |
| 4.5 | 8.23 | 0.0 | 0 | 0 | 0 | 97 | 97 | 97 |
| 6 | 8.19 | 0.0 | 0 | 0 | 0 | 97 | 97 | 97 |

TABLE 20

5.1% Pt-1% Bi/C(3SW) - Bi/Pt = 0.2-4 eq Na₂CO₃

| Time [h] | pH | HMF [mM] | HMFCA [mM] | DFF [mM] | FFCA [mM] | FDCA [mM] | MB [mM] | TOC [mM] |
|---|---|---|---|---|---|---|---|---|
| 0 | 10.66 | 97 | 0 | 0 | 0 | 0 | 97 | 98 |
| 0.25 | 9.76 | 18 | 7 | 0 | 23 | 44 | 92 | * |
| 0.5 | 9.50 | 0 | 2 | 0 | 10 | 82 | 95 | * |
| 1 | 9.44 | 0 | 0 | 0 | 2 | 92 | 94 | * |
| 2 | 9.40 | 0 | 0 | 0 | 0 | 95 | 95 | 94 |
| 3 | 9.36 | 0 | 0 | 0 | 0 | 95 | 95 | * |
| 4 | 9.33 | 0 | 0 | 0 | 0 | 96 | 96 | 95 |
| 5 | 9.31 | 0 | 0 | 0 | 0 | 95 | 95 | * |
| 6 | 9.30 | 0 | 0 | 0 | 0 | 96 | 96 | 95 |
| 8 | 9.28 | 0 | 0 | 0 | 0 | 96 | 96 | * |
| 12 | 9.26 | 0 | 0 | 0 | 0 | 97 | 97 | 95 |

The results show that the type of cation does not have any influence but that the replacement of 4 equivalents of weak bases NaHCO₃ or KHCO₃ by 2 equivalents of more basic weak bases such as Na₂CO₃ or K₂CO₃ leads to a significant increase in reaction speeds which are completed in a little over 2 h 30 with quantitative FDCA yield. The adding of 4 equivalents of Na₂CO₃ further accelerates the reaction which is then completed in less than 2 hours.

EXAMPLE 6 (ACCORDING TO THE INVENTION)

Comparison Between 2 Modes for the Preparation of Bimetallic PtBi/C Catalysts

The activity of two bimetallic catalysts prepared in accordance with two modes, ex-situ and in-situ, was compared under standard conditions of the reaction with Na₂CO₃/HMF ratio of 2. The entirety of the added bismuth was deposited on the monometallic Pt/C catalyst if the bismuth salt used was soluble in an alkaline medium (e.g. (Bi(NO₃)₃, 5H₂O). Tables 21 and 22 summarise the results obtained with the two different preparation modes:

TABLE 21

3.6% Pt0.68% Bi/C(L3S) - in-situ Bi/Pt = 0.19

| Time [h] | HMF [mM] | % C HMF | FFCA [mM] | % Y FFCA | FDCA [mM] | % Y FDCA |
|---|---|---|---|---|---|---|
| 0 | 98 | 0 | 0 | 0 | 0 | 0 |
| 0.25 | 13 | 87 | 38 | 39 | 31 | 32 |
| 0.5 | 0 | 100 | 24 | 25 | 67 | 68 |
| 1 | 0 | 100 | 11 | 12 | 83 | 85 |
| 2 | 0 | 100 | 4 | 4 | 93 | 94 |
| 3 | 0 | 100 | 1 | 1 | 96 | 98 |
| 4 | 0 | 100 | 0 | 0 | 98 | 100 |
| 5 | 0 | 100 | 0 | 0 | 98 | 100 |
| 6 | 0 | 100 | 0 | 0 | 98 | 100 |

TABLE 22

5.1% Pt1% Bi/C(3SW) - ex-situ Bi/Pt = 0.2

| Time [h] | HMF [mM] | % C HMF | FFCA [mM] | % Y FFCA | FDCA [mM] | % Y FDCA |
|---|---|---|---|---|---|---|
| 0 | 96 | 0 | 0 | 0 | 0 | 0 |
| 0.16 | 8 | 92 | 59 | 62 | 17 | 18 |
| 0.33 | 0 | 100 | 42 | 44 | 47 | 49 |
| 0.5 | 0 | 100 | 29 | 30 | 63 | 66 |
| 1 | 0 | 100 | 16 | 17 | 79 | 83 |
| 2 | 0 | 100 | 4 | 4 | 91 | 95 |
| 3 | 0 | 100 | 0 | 0 | 95 | 99 |
| 4 | 0 | 100 | 0 | 0 | 95 | 100 |
| 6 | 0 | 100 | 0 | 0 | 96 | 100 |

The results show that irrespective of the preparation modes of the bimetallic catalyst, provided a Bi precursor salt soluble in an alkaline medium is chosen, the activity of the bimetallic catalyst remains comparable.

EXAMPLE 7 (ACCORDING TO THE INVENTION)

Influence of Temperature

The method such as described above was implemented with the 5.1% Pt-1% Bi/C(3SW) catalyst (Bi/Pt=0.2), with Na₂CO₃/HMF molar ratio=2 and at a temperature of between 80 and 120° C.

The results are grouped together in Tables 23 to 25 below:

TABLE 23

100° C.

| Time [h] | HMF [mM] | % C HMF | FFCA [mM] | % Y FFCA | FDCA [mM] | % Y FDCA |
|---|---|---|---|---|---|---|
| 0 | 96 | 0 | 41 | 43 | 0 | 0 |
| 0.1667 | 8 | 91 | 59 | 62 | 17 | 18 |
| 0.3333 | 0 | 100 | 42 | 44 | 47 | 49 |
| 0.5 | 0 | 100 | 29 | 30 | 63 | 66 |
| 1 | 0 | 100 | 16 | 17 | 79 | 83 |
| 2 | 0 | 100 | 4 | 4 | 91 | 95 |
| 3 | 0 | 100 | 0 | 0 | 95 | 99 |
| 4 | 0 | 100 | 0 | 0 | 95 | 100 |
| 5 | 0 | 100 | 0 | 0 | 96 | 100 |
| 6 | 0 | 100 | 0 | 0 | 96 | 100 |
| 10 | 0 | 100 | 0 | 0 | 96 | 100 |

TABLE 24

80° C.

| Time [h] | HMF [mM] | % C HMF | FFCA [mM] | % Y FFCA | FDCA [mM] | % Y FDCA |
|---|---|---|---|---|---|---|
| 0 | 100 | 0 | 0 | 0 | 0 | 0 |
| 0.25 | 20 | 80 | 50 | 50 | 18 | 18 |
| 0.5 | 0 | 100 | 46 | 46 | 43 | 43 |
| 1 | 0 | 100 | 29 | 29 | 65 | 65 |
| 2 | 0 | 100 | 14 | 14 | 83 | 83 |
| 3 | 0 | 100 | 9 | 9 | 90 | 90 |
| 4 | 0 | 100 | 4 | 4 | 95 | 95 |
| 6 | 0 | 100 | 1 | 1 | 98 | 98 |
| 8 | 0 | 100 | 0 | 0 | 99 | 99 |
| 10 | 0 | 100 | 0 | 0 | 99 | 99 |
| 12 | 0 | 100 | 0 | 0 | 99 | 99 |

TABLE 25

120° C.

| Time [h] | HMF [mM] | % C HMF | FFCA [mM] | % Y FFCA | FDCA [mM] | % Y FDCA |
|---|---|---|---|---|---|---|
| 0 | 97 | 0 | 0 | 0 | 0 | 0 |
| 0.1 | 38 | 61 | 43 | 44 | 4 | 4 |

TABLE 25-continued

120° C.

| Time [h] | HMF [mM] | % C HMF | FFCA [mM] | % Y FFCA | FDCA [mM] | % Y FDCA |
|---|---|---|---|---|---|---|
| 0.2 | 5 | 95 | 50 | 51 | 37 | 38 |
| 0.4 | 0 | 100 | 22 | 23 | 73 | 76 |
| 0.6 | 0 | 100 | 10 | 11 | 87 | 90 |
| 0.8 | 0 | 100 | 6 | 6 | 91 | 93 |
| 1 | 0 | 100 | 3 | 3 | 94 | 97 |
| 1.5 | 0 | 100 | 1 | 1 | 95 | 98 |
| 2 | 0 | 100 | 0 | 0 | 96 | 99 |
| 2.5 | 0 | 100 | 0 | 0 | 97 | 100 |
| 3 | 0 | 100 | 0 | 0 | 97 | 100 |
| 5 | 0 | 100 | 0 | 0 | 96 | 99 |
| 12 | 0 | 100 | 0 | 0 | 96 | 99 |

An increase in temperature allows an increase in reaction speed provided a temperature of 160° C. is not exceeded, over and above which HMF degradation reactions may occur.

EXAMPLE 8 (ACCORDING TO THE INVENTION)

Influence of Pressure

The method such as described above was implemented with the 5.1% Pt-1% Bi/C(3SW) catalyst (Bi/Pt=0.2), with $Na_2CO_3$/HMF molar ratio=2 at a temperature of 100° C. and air pressure of 50 bar and 60 bar.

TABLE 26

50 bar

| Time [h] | HMF [mM] | % C HMF | FFCA [mM] | % Y FFCA | FDCA [mM] | % Y FDCA |
|---|---|---|---|---|---|---|
| 0 | 99 | 0 | 0 | 0 | 0 | 0 |
| 0.25 | 26 | 76 | 35 | 35 | 27 | 28 |
| 0.5 | 0 | 100 | 31 | 32 | 63 | 64 |
| 1 | 0 | 100 | 14 | 15 | 83 | 84 |
| 2 | 0 | 100 | 6 | 6 | 92 | 93 |
| 3 | 0 | 100 | 2 | 2 | 97 | 98 |
| 4 | 0 | 100 | 0 | 0 | 98 | 99 |
| 5 | 0 | 100 | 0 | 0 | 98 | 99 |
| 6 | 0 | 100 | 0 | 0 | 98 | 99 |
| 10 | 0 | 100 | 0 | 0 | 98 | 99 |

The results obtained with air pressure of 60 bar were similar to those obtained at 50 bar, and show that a pressure over and above 40 bar has no influence on the reaction.

EXAMPLE 9 (ACCORDING TO THE INVENTION)

Recycling of the Bimetallic PtBi Catalyst

The stability of the 3.6% Pt-0.9% Bi/C(L3S) catalyst, (Bi/Pt=0.25) was evaluated in the presence of $NaHCO_3$ as base with $NaHCO_3$/HMF molar ratio of 4, by recycling the catalyst three times: 1st cycle with the new catalyst then 3 separate cycles with the same catalyst after washing in water and oven drying in air at 100° C. without any reducing treatment. The results are grouped together in the Tables below:

TABLE 27

1st cycle

| Time [h] | HMF [mM] | % HMF | FFCA [mM] | % FFCA | FDCA [mM] | % FDCA |
|---|---|---|---|---|---|---|
| 0 | 103 | 0 | 0 | 0 | 0 | 0 |
| 0.16 | 55 | 47 | 29 | 28 | 1 | 1 |
| 0.33 | 13 | 87 | 64 | 63 | 8 | 8 |
| 0.5 | 0 | 100 | 70 | 68 | 18 | 18 |
| 0.75 | 0 | 100 | 63 | 61 | 29 | 29 |
| 1 | 0 | 100 | 56 | 55 | 38 | 37 |
| 2 | 0 | 100 | 38 | 36 | 60 | 59 |
| 3 | 0 | 100 | 19 | 18 | 80 | 78 |
| 4 | 0 | 100 | 10 | 10 | 89 | 86 |
| 6 | 0 | 100 | 3 | 3 | 96 | 94 |
| 8 | 0 | 100 | 1 | 1 | 99 | 96 |
| 10 | 0 | 100 | 0 | 0 | 100 | 97 |
| 12 | 0 | 100 | 0 | 0 | 101 | 98 |

TABLE 28

2nd cycle

| Time [h] | HMF [mM] | % HMF | FFCA [mM] | % FFCA | FDCA [mM] | % FDCA |
|---|---|---|---|---|---|---|
| 0 | 100 | 10 | 0 | 0 | 0 | 0 |
| 0.25 | 64 | 36 | 19 | 19 | 1 | 1 |
| 0.5 | 22 | 78 | 53 | 53 | 7 | 7 |
| 0.75 | 4 | 96 | 66 | 66 | 16 | 16 |
| 1 | 0 | 100 | 64 | 63 | 24 | 24 |
| 2 | 0 | 100 | 47 | 47 | 47 | 47 |
| 3 | 0 | 100 | 33 | 33 | 65 | 64 |
| 4.1 | 0 | 100 | 22 | 22 | 76 | 76 |
| 6 | 0 | 100 | 12 | 12 | 88 | 87 |
| 8 | 0 | 100 | 4 | 4 | 97 | 96 |
| 10.1 | 0 | 100 | 1 | 1 | 99 | 99 |
| 12 | 0 | 100 | 0 | 0 | 100 | 100 |

TABLE 29

3rd cycle

| Time [h] | HMF [mM] | % HMF | FFCA [mM] | % FFCA | FDCA [mM] | % FDCA |
|---|---|---|---|---|---|---|
| 0 | 100 | 0 | 0 | 0 | 0 | 0 |
| 0.25 | 68 | 32 | 17 | 17 | 1 | 1 |
| 0.5 | 28 | 72 | 49 | 49 | 6 | 6 |
| 0.75 | 4 | 96 | 66 | 66 | 17 | 17 |
| 1 | 0 | 100 | 63 | 63 | 25 | 25 |
| 2 | 0 | 100 | 48 | 47 | 48 | 48 |
| 3 | 0 | 100 | 33 | 33 | 66 | 66 |
| 4 | 0 | 100 | 23 | 23 | 76 | 76 |
| 6 | 0 | 100 | 12 | 12 | 90 | 90 |
| 8.1 | 0 | 100 | 4 | 4 | 97 | 97 |
| 10 | 0 | 100 | 2 | 2 | 100 | 100 |
| 12 | 0 | 100 | 0 | 0 | 100 | 100 |

TABLE 30

4th cycle

| Time [h] | HMF [mM] | % HMF | FFCA [mM] | % FFCA | FDCA [mM] | % FDCA |
|---|---|---|---|---|---|---|
| 0 | 99 | 0 | 0 | 0 | 0 | 0 |
| 0.25 | 72 | 27 | 15 | 15 | 1 | 1 |
| 0.5 | 44 | 56 | 38 | 38 | 4 | 4 |
| 0.75 | 16 | 84 | 61 | 62 | 11 | 11 |
| 1 | 2 | 98 | 68 | 69 | 19 | 19 |
| 2 | 0 | 100 | 60 | 60 | 35 | 36 |
| 3 | 0 | 100 | 48 | 48 | 48 | 49 |

TABLE 30-continued

| | | | 4th cycle | | | |
|---|---|---|---|---|---|---|
| Time [h] | HMF [mM] | % HMF | FFCA [mM] | % FFCA | FDCA [mM] | % FDCA |
| 4 | 0 | 100 | 38 | 38 | 59 | 60 |
| 6 | 0 | 100 | 21 | 22 | 76 | 76 |
| 8 | 0 | 100 | 11 | 11 | 87 | 88 |
| 10 | 0 | 100 | 5 | 5 | 93 | 94 |
| 12 | 0 | 100 | 0 | 0 | 98 | 99 |

The results show that the bimetallic PtBi/C catalyst does not significantly lose its activity, contrary to the monometallic Pt/C catalyst (Example 3) which requires a new reduction before each re-use so that it is able to keep its good catalytic activity.

EXAMPLE 10 (ACCORDING TO THE INVENTION)

Influence of Catalyst Weight

The method such as described above was implemented at 120° C. using twice less catalyst (HMF/Pt=200) in the presence of 2 equivalents of $Na_2CO_3$ with the 5.1% Pt1% Bi/C(3SW) catalyst. The FDCA yield was always above 95% with a reaction time of less than 8 h.

The invention claimed is:

1. A method for preparing 2,5-furandicarboxylic acid (FDCA) by oxidizing 5-hydroxymethylfurfural (HMF) in water in the presence of a weak base and a supported catalyst comprising platinum and bismuth, wherein the Bi/Pt molar ratio in the catalyst is between 0.1 and 0.3.

2. The method according to claim 1, wherein the reaction medium does not comprise an organic solvent.

3. The method according to claim 1, wherein the amount of platinum in the catalyst is between 1% and 10% by weight relative to the weight of the supported catalyst.

4. The method according to claim 1, wherein the weak base is selected from among bases having a pKb value higher than 1.4.

5. The method according to claim 1, wherein the weak base is selected from among the carbonates and hydrogen carbonates of alkaline metals, either alone or in a mixture.

6. The method according to claim 1, wherein the method is implemented under pressure so as to obtain a $O_2$/HMF molar ratio higher than 2.

7. The method according to claim 1, conducted at a temperature of 70 to 150° C.

8. The method according to claim 1, wherein the weak base/HMF molar ratio is 1 or higher.

9. The method according to claim 1, wherein the HMF/Pt molar ratio is between 50 and 400.

10. The method of claim 1, wherein the Bi/Pt molar ratio in the catalyst is between 0.15 and 0.3.

11. The method of claim 3, wherein the amount of platinum in the catalyst is between 3% and 6% by weight relative to the weight of the supported catalyst.

12. The method of claim 5, wherein the carbonates and hydrogen carbonates of alkaline metals are chosen from sodium and potassium carbonates and hydrogen carbonates.

13. The method of claim 1, conducted at a temperature between 80 and 120° C.

* * * * *